(12) United States Patent
Maggio et al.

(10) Patent No.: US 12,053,165 B1
(45) Date of Patent: Aug. 6, 2024

(54) URINE COLLECTION SYSTEM AND METHOD OF COLLECTING URINE

(71) Applicants: Denise Angela Maggio, Fort Mill, SC (US); Alexander Daniel Maggio, Fort Mill, SC (US); Austin Kenneth Maggio, Fort Mill, SC (US)

(72) Inventors: Denise Angela Maggio, Fort Mill, SC (US); Alexander Daniel Maggio, Fort Mill, SC (US); Austin Kenneth Maggio, Fort Mill, SC (US)

(73) Assignee: CLEANCATCH SOLUTIONS INC., Wilmington, DE (US)

( * ) Notice: Subject to any disclaimer, the term of this patent is extended or adjusted under 35 U.S.C. 154(b) by 0 days.

(21) Appl. No.: 18/541,529

(22) Filed: Dec. 15, 2023

Related U.S. Application Data

(60) Provisional application No. 63/527,359, filed on Jul. 18, 2023.

(51) Int. Cl.
*A61B 10/00* (2006.01)

(52) U.S. Cl.
CPC .................................. *A61B 10/007* (2013.01)

(58) Field of Classification Search
CPC ....... A61B 10/007; A61F 5/4556; A61F 5/455
See application file for complete search history.

(56) References Cited

U.S. PATENT DOCUMENTS

| | | | |
|---|---|---|---|
| 3,232,657 A | 2/1966 | Secoy et al. | |
| 5,174,965 A | 12/1992 | Jones et al. | |
| 5,226,551 A * | 7/1993 | Robbins, III | B65D 1/0292 220/666 |
| 5,445,022 A | 8/1995 | Vassallo | |
| 5,492,220 A | 2/1996 | Estay | |
| 5,558,840 A | 9/1996 | Jones et al. | |
| 5,788,298 A | 8/1998 | Cheng | |
| 5,920,916 A * | 7/1999 | Norton | A61B 10/007 4/144.3 |
| 6,485,438 B1 | 11/2002 | Minue | |
| 6,719,951 B1 * | 4/2004 | Griffith | A61B 10/007 215/396 |
| 6,799,694 B1 | 10/2004 | Scott | |
| 7,000,963 B2 | 2/2006 | Dodd et al. | |
| 8,465,440 B1 | 6/2013 | Grayson | |
| 9,662,094 B2 | 5/2017 | Meloff et al. | |

(Continued)

*Primary Examiner* — Alex M Valvis
*Assistant Examiner* — Nidhi N Patel
(74) *Attorney, Agent, or Firm* — Invention To Patent Services; Alex Hobson

(57) ABSTRACT

A urine collection system provides a method of collecting urine in a safe and ergonomic manner having a handle that extends from the urine collector to enable much more ergonomic positioning during urine collection. The handle is detachable from the urine collector. Also, the urine collection system includes a lid that is configured to fit over the collector opening of the urine collector to prevent spilling of the urine, or contact of the urine during processing. The urine collector includes a container having a collection funnel portion forming the collector opening to the urine collector and a retainer portion, coupled to the collection funnel portion. The collection funnel portion may be detachable from the retainer portion and the retainer portion may be a cup with a threaded lid that is removed to attach the cup to the collection funnel portion.

14 Claims, 9 Drawing Sheets

(56) References Cited

U.S. PATENT DOCUMENTS

| | | |
|---|---|---|
| 10,335,121 B2 * | 7/2019 | Desai .................... A61B 10/007 |
| 11,221,278 B2 | 1/2022 | Briseno |
| 2002/0009346 A1 | 1/2002 | Holt |
| 2005/0010189 A1 * | 1/2005 | Toomey ........... A61B 5/150389 |
| | | 604/403 |
| 2005/0081793 A1 * | 4/2005 | Sannikka ............. A61B 10/007 |
| | | 119/165 |
| 2009/0124929 A1 * | 5/2009 | Rossi-Pipitone .... A61B 10/007 |
| | | 600/574 |
| 2011/0071434 A1 | 3/2011 | Higgins |
| 2011/0165039 A1 | 7/2011 | Khoury |
| 2013/0143226 A1 * | 6/2013 | Hill .................... A61B 10/0045 |
| | | 600/583 |
| 2016/0089118 A1 | 3/2016 | Petersilia |

\* cited by examiner

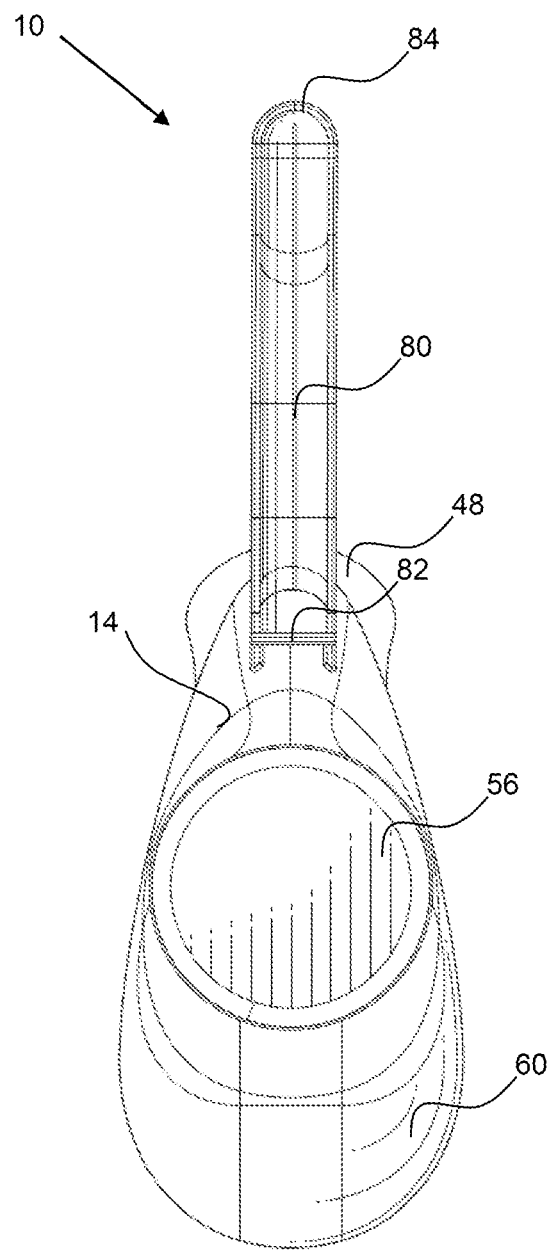
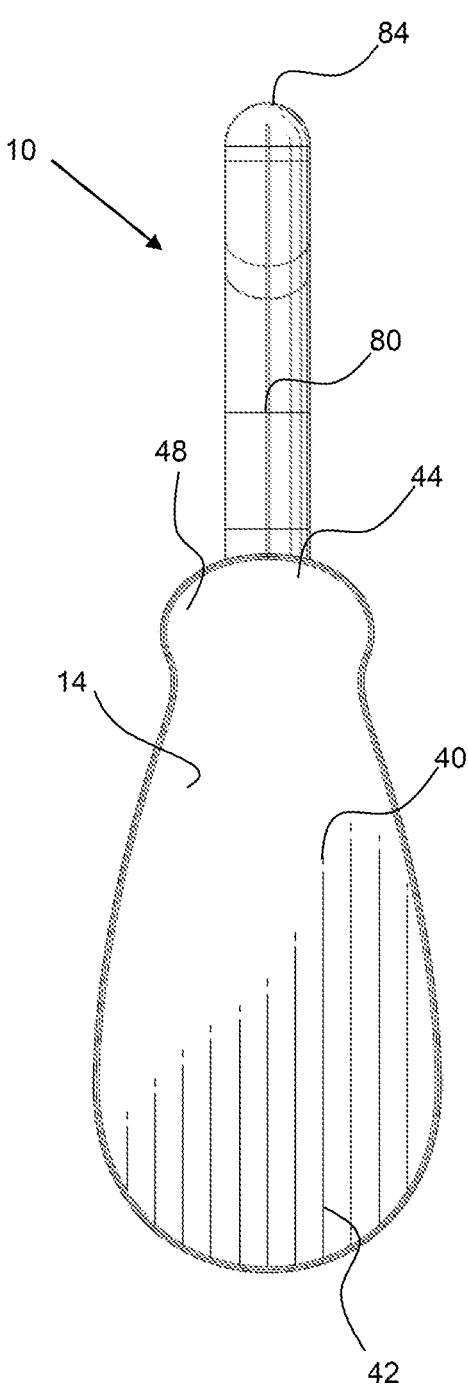
FIG. 8
FIG. 9

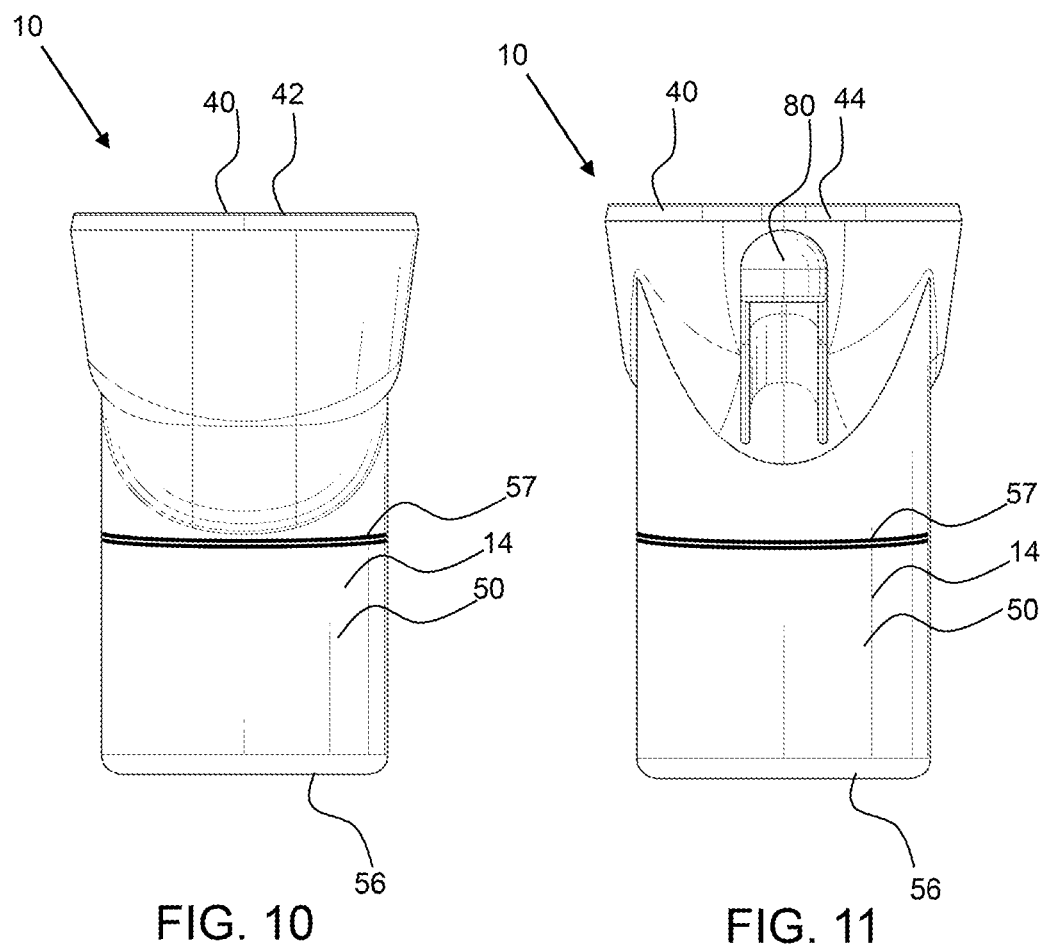

URINE COLLECTION SYSTEM AND METHOD OF COLLECTING URINE

CROSS REFERENCE TO RELATED APPLICATIONS

This application claims the benefit of priority to U.S. provisional patent application No. 63/527,359 filed on Jul. 18, 2023; the entirety of which is hereby incorporated by reference herein.

BACKGROUND OF THE INVENTION

Field of the Invention

The invention relates to a urine collection system and method of collecting urine in a safe and ergonomic manner.

Background

It is difficult for females to provide a urine sample, wherein they have to position themselves over a toilet and then hold the collection cup underneath them which requires an awkward position. Also, urine often gets on the woman's hand during the collection. Furthermore, women that are going through chemotherapy have toxic urine. The chemicals used during chemotherapy affect the urine such that is can be gene altering. Therefore, collection of urine in a more controlled manner that is more ergonomic and precise, wherein there is not urine on the outside of the container, would be preferred.

SUMMARY OF THE INVENTION

The invention is directed to a urine collection system and method of collecting urine in a safe and ergonomic manner. An exemplary urine collection system has a handle that is detachably attachable to the urine collector. The handle enables much more ergonomic position of the urine collector during urine collection as it extends from the urine collector proximal to the top or to collector opening. Urine may be collected in the urine collector and then the handle can be detached before being turned in for analysis. Also, the urine collection system includes a lid that is configured to fit over the collector opening of the urine collector to prevent spilling of the urine, or contact of the urine during processing. The urine collector includes a container having a collection funnel portion forming the collector opening to the urine collector and a retainer portion, coupled to the collection funnel portion and extending to a base. The collection funnel portion may be shaped to aid in collection of urine from a woman having a bulbous end and a tapered end. The retainer portion may be regular shaped, such as being cylindrical in shape and may be much smaller in cross-sectional dimension than the length of the collection funnel portion to aid in insertion of the urine collector through an opening between a person and the front edge or front portion of the seat of a toilet.

The handle is configured to extend from the urine collector an extended distance that is a suitable and effective length to provide a more comfortable position for holding by hand during urine collection. The length of the handle from the connected end to the extended end may be about 8 cm or more, about 10 cm or more about 12 cm or more, about 15 cm or more, about 20 cm or more and any range between and including the distance values provided. The handle may extend horizontally away from the urine collector when the urine collector is resting on the base on a horizontal surface and may extend an extended distance from the base or retainer portion that may be about 10 cm or more, about 12 cm or more, about 15 cm or more, about 20 cm or more and any range between and including the extended distance values provided. The handle may extend an offset distance vertically from the connected end to the extended end of the handle and this offset distance may be 2 cm or more, about 5 cm or more, about 8 cm or more, about 10 cm or more and any range between and including the distance values provided. Also, the top of the handle may be configured a vertical offset from the collector opening or top of the urine collector a small distance, such as about 1 cm or less, about 2 cm or less, about 4 cm or less, about 8 cm or less and any range between and including the distance values provided. This vertical offset distance and extended distance may help ensure that no urine splashes onto the user's hand during use.

The handle may be coupled to the urine collector on the retainer portion or on the collection funnel portion. It may be preferred that the handle is coupled to the collection funnel portion and extend above the top of the urine collector or have an extended end that is has a very small vertical offset distance from the top of the urine collector as described herein.

A handle may be detachably attachable having a handle-connector configured to attach to the collector-connector of a urine collector. The collector-connector may be configured on the extended end of a connector extension for ease of use. The handle connection to the urine collector or collector-connector may be a dove-tail connection. A dove-tail connection may include dove-tail in one component of the dove-tail connection and dove-tail slot flanges configured to slide into the receiver slots formed by the dove-tail. A dove-tail has a dove-tail extension and dove-tail flanges that extend out orthogonally from the dove-tail extension and the receiver slots are formed under these dove-tail flanges and along the dove-tail extension. A pair of dove-tail slot-flanges may be configured to slide into the receiver-slots to form a dove-tail connection. In an exemplary embodiment, the handle connector has dove-tail slot-flanges that extend inward along a handle cavity such as along the extended end of the handle. An insertion gap configured between the two dove-tail slot-flanges enables the dove-tail slot-flanges to be slid along the receiver-slots of the dove-tail of the collector-connector to detachably attach the handle to the urine collector.

A handle may also be a frangible handle having a frangible feature that enables the handle to be easily detached from the urine collector. A frangible feature is an abrupt reduction in cross-sectional area of the handle along the length of the handle, or a slit and the handle may include a single slit or a plurality of slits. In an exemplary embodiment, a pair of slits are configured on opposing sides of the handle. In an exemplary embodiment, the slit or pair of slits on opposing sides are configured on the sides of the handle, versus the top or bottom, such that the handle maintains strength for supporting the urine collector, even when containing urine. The frangible feature may be coupled to proximal to the connected end of the handle to the urine collector or about 25 mm or less from the connected end, or about 15 mm or less, or about 10 mm or less, or even 5 mm or less from the connected end with the urine collector.

An exemplary collection funnel portion has a bulbous end and a tapered end, that tapers in width across the opening from the bulbous end. The collection funnel portion is therefore egg-shaped or forms an egg-shaped opening to urine collector. The bulbous end may extend along a radius of curvature along the collector opening and then funnel down from the collector opening to the retainer portion. The bulbous end may be much wider than the tapered end, such as about 1.25 times or more, about 1.5 times or more, about 1.75 times or more, about 2 times or more and any range between and including the ratios provided.

A lid is configured for placement over the urine collector and is secured over the opening. The exemplary lid has a shape that conforms with the collection funnel portion opening and has a bulbous end and a tapering end, that tapers from the bulbous end of the lid. The lid is egg-shaped. Also, the lid may have a lid-handle extending from the exterior surface.

The retainer portion is coupled to the collection funnel portion along a connected end and extends to a base or bottom that is planar to allow the urine collector to rest upright on flat surface, such as a counter or table.

The urine collector has an interior surface along the collection funnel portion to funnel urine down into the retainer portion, along the interior surface of the retainer portion. The retainer portion has an exterior surface that may be cylindrical in shape and the collection funnel portion has an exterior surface that may also be tapering or funneling from the collector opening down to the connected end with the retainer portion. The lid also has an exterior surface and an interior surface.

The urine collector including the retainer portion and the collection funnel portion may be a one-piece unit, such as a part that is molded together, such as through injection molding and may be a monolithic part. Alternatively, the retainer portion may be detachably attachable to the collection funnel portion by a connector. A connector may be threads, such as male threads that thread into female threads, a snap on connector, such as a rim that snaps over a flange ring and the like. In an exemplary embodiment, the connector is male threads on the retainer portion and female threads on the interior of the collection funnel portion of the urine collector. The male threads of the retainer portion may be configured to retain a lid on the retainer portion and this lid may be removed before the collection funnel portion is threaded thereon. The retainer portion may be a conventional urine collection cup and may be provided with a lid detachably attached thereon. The lid may have threads and may thread onto the threads of the cup or retainer portion of the urine collector. The lid may keep the interior of the cup clean prior to use for urine collection.

The retainer portion may be cylindrical in shape having an outer diameter of about 4 cm or more, about 5 cm or more, about 6 cm or more, about 8 cm or more, about 10 cm or more about 12 cm or less, about 10 cm or less and any range between and including the dimensions provided. The height of the retainer portion of the urine collector may be about 8 cm or more, about 10 cm or more, about 12 cm or more, about 14 cm or more and any range between and including the dimensions provided.

The collection funnel portion may have a length from the tapered end to the bulbous end of about 8 cm or more, about 10 cm or more, about 12 cm or more, about 14 cm or more, about 16 cm or more and any range between and including the values provided. The bulbous end of the collection funnel portion may have a width across orthogonal to the length axis at the collector opening of about 4 cm or more, about 5 cm or more, about 6 cm or more, about 8 cm or more, about 10 cm or more and any range between and including the values provided. The tapered end of the collection funnel portion may have a width along the collector opening and taken about 30 mm from the tapered end of about 3 cm or more, about 4 cm or more, about 5 cm or more, about 6 cm or more. Again, the width of the bulbous end may be much wider than the width of the tapered end along the collector opening.

The handle may have a length from a connected end to an extended end of about 8 cm or more, about 10 cm or more, about 12 cm or more, about 14 cm or more, about 16 cm or more and any range between and including the values provided. A length of at least 10 cm or more, and preferably about 12 cm or more enables easier positioning of the urine collection during use.

The urine collection system including the urine collector and the handle may be made out of plastic and the assembly may be injection molded. The handle may however, be coupled to the urine collector in a separate step and the frangible feature may be formed during the connection of the handle to the urine collector.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

FIG. 8 shows a bottom view of the urine collector with the handle detachably attached to the collector-connector.

FIG. 9 shows a top view of the urine collector with a lid over the top opening and a handle detachably attached to the collector-connector.

FIG. 10 shows a back view of the urine collector with a lid over the top opening.

FIG. 11 shows a front view of the urine collector with a lid over the top opening and a handle detachably attached to the collector-connector.

Figure 1:
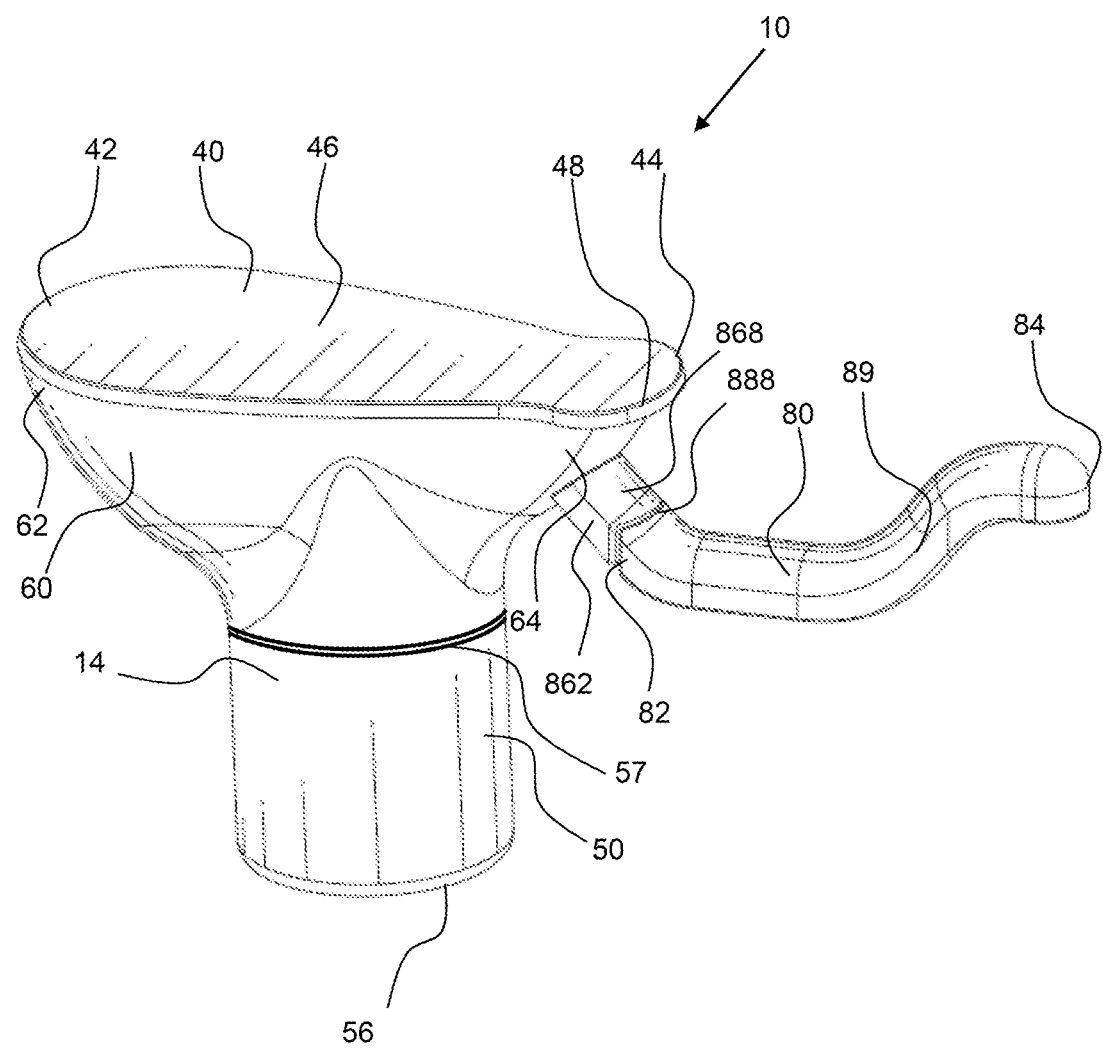
FIG. 1 shows a perspective view of urine collection system having a handle connected to a urine collector by a dove-tail connection and a lid over the opening to the urine collector.

Corresponding reference characters indicate corresponding parts throughout the several views of the figures. The figures represent an illustration of some of the embodiments of the present invention and are not to be construed as limiting the scope of the invention in any manner. Some of the figures may not show all of the features and components of the invention for ease of illustration, but it is to be understood that where possible, features and components from one figure may be included in the other figures. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Figure 3:
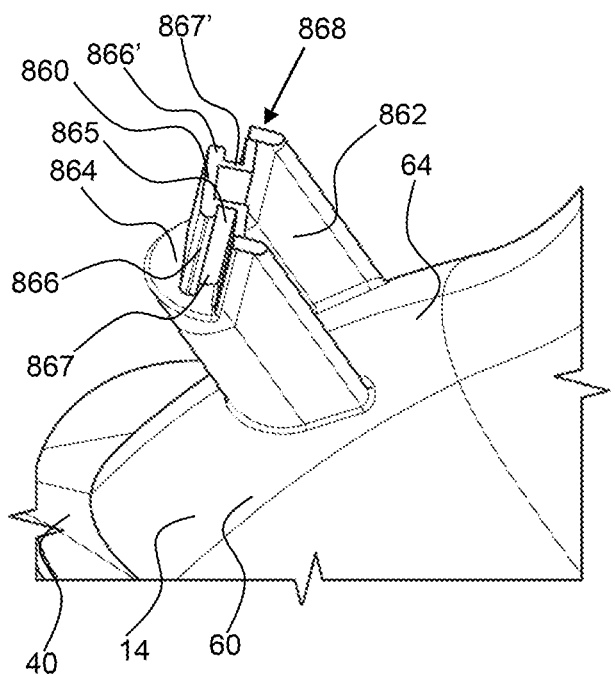
FIG. 3 shows a perspective view of collector-connector having a receiver slot along a dove-tail extension and dove-tail flanges extending over the dove-tail extension to form said receiver-slots.
Figure 4:
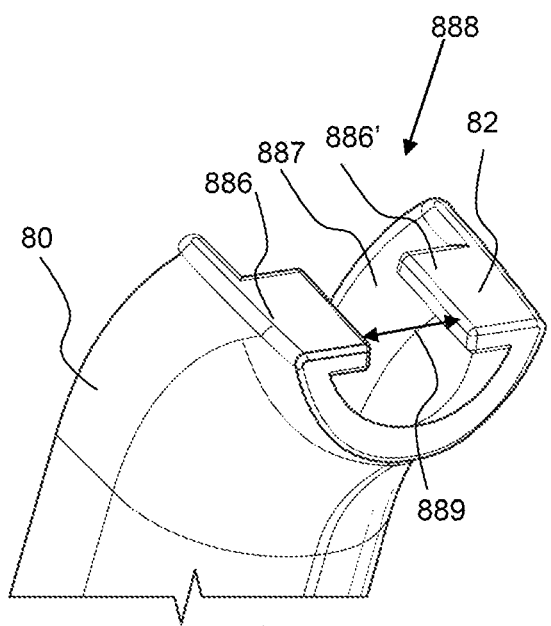
FIG. 4 shows a perspective view of the connected end of the handle having a handle connector configured to detachably attach with the dove-tail shown in FIG. 3, and having dove-tail slot-flanges configured to slide along the receiver slot of the dove-tail of the collector-connector.
Figure 5:
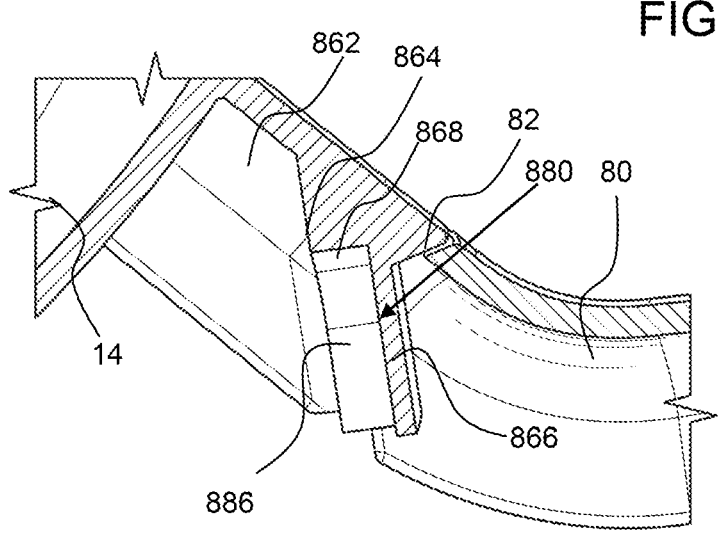
FIG. 5 shows a cross-sectional view of the dove-tail connection between the handle-connector and the collector-connector.
Figure 12:
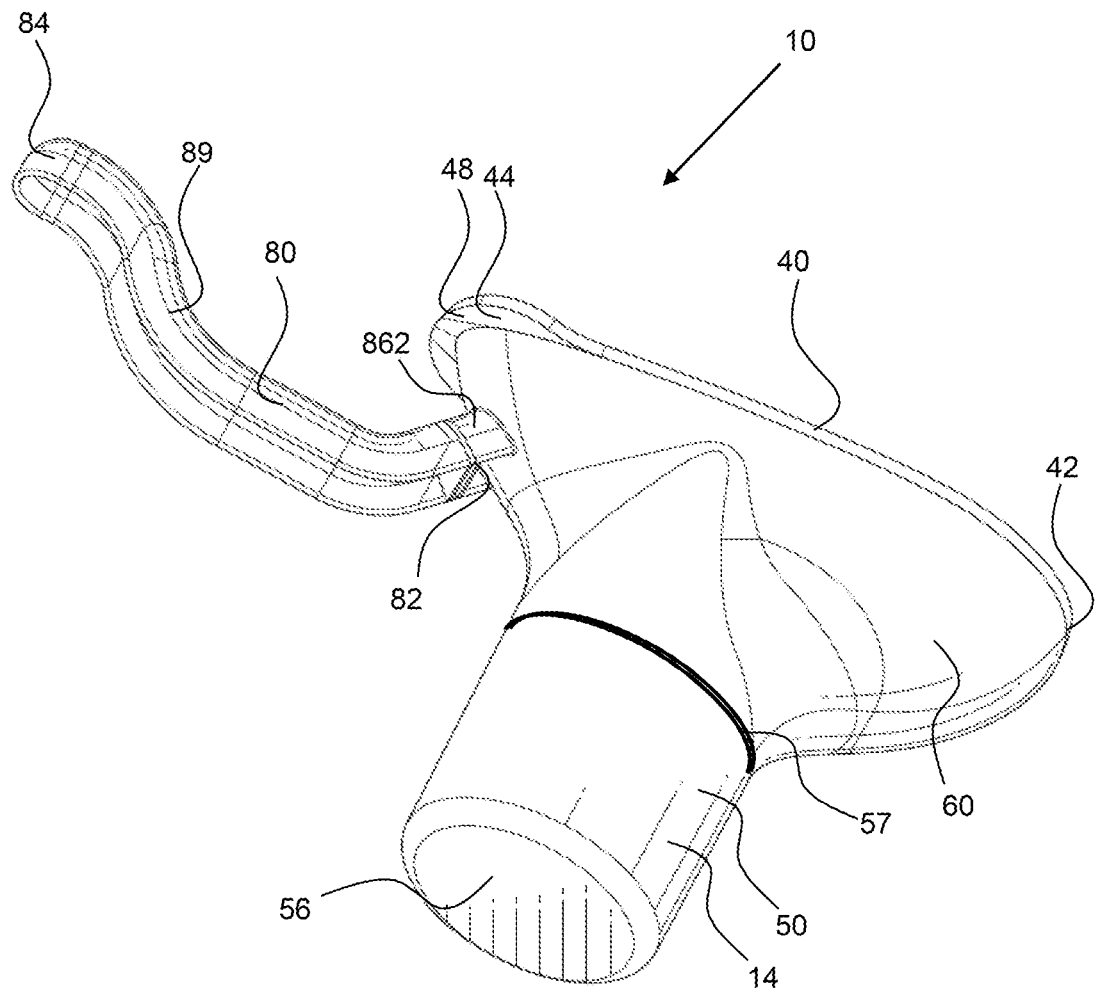
FIG. 12 shows a perspective view of the urine collector with a lid over the top opening and a handle detachably attached to the collector-connector.

Referring now to FIGS. 1 to 14, an exemplary urine collection system 10 has a handle 80 connected to a urine collector 14 by a dove-tail connection 880. As shown in FIGS. 1 and 3-12, a lid 40 configured over the collector opening 61 to the urine collector and has an overhang that acts as a lid-handle 48, as best shown in FIG. 12. The lid 40 is removed from the urine collector 14 to expose the collector opening 61 as shown in FIG. 2. The urine collector 14 has a collection funnel portion 60 that directs and funnels urine down into the retainer portion 50, which may be cylindrical in shape as shown. The collection funnel portion 60 has a bulbous end 62 and a tapered end 64, that tapers in width across the opening from the bulbous end, as best shown in FIG. 8. The collection funnel portion is therefore egg-shaped or forms an egg-shaped opening to urine collector. A lid 40 is configured for placement over the urine collector 14 and is secured over the collector opening 61. The exemplary lid 40 has a shape that conforms with the collection funnel portion collector opening 61 and has a bulbous end 42 and a tapering end 44, that tapers from the bulbous end 42 of the lid 40. The lid is egg-shaped. Also, the lid 40 has a lid-handle 48 or extension that extends out from the urine collector 14 to enable a person to grab and pull the lid off. The exterior surface of the lid 46 may be planar as shown. As shown in FIGS. 3 to 5, the handle 80 is detachable from the urine collector 14 by a dove-tail connection 880.

Figure 2:
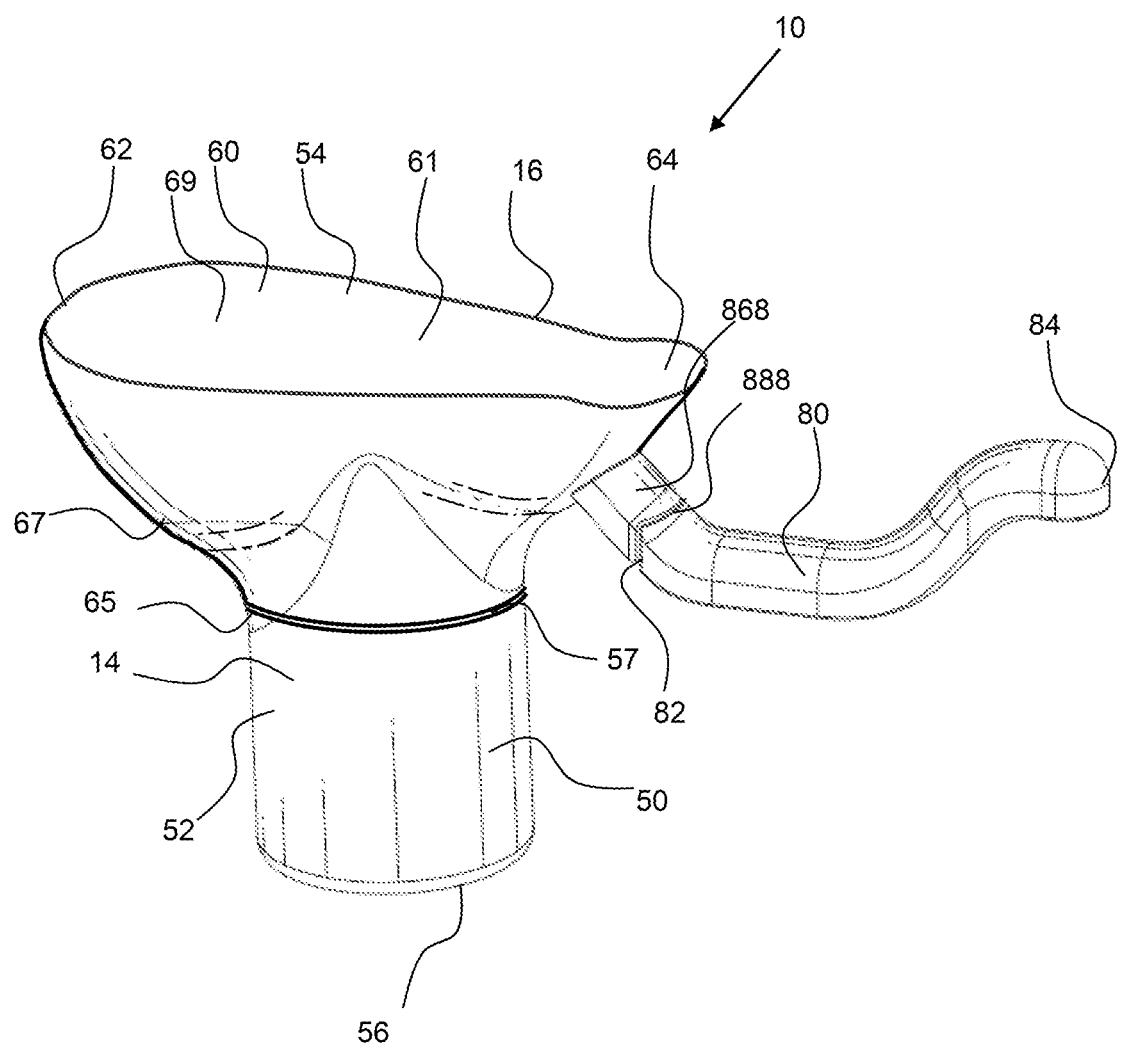
FIG. 2 shows a perspective view of the urine collection system shown in FIG. 1, with the lid removed to show the top opening of the urine collector.

Referring now to FIGS. 1 and 2, the urine collection system 10 includes a urine collector 14, a lid 40 and a detachably attachable handle 80. The lid is configured over the collector opening 61 in FIG. 1 and is removed in FIG. 2. The handle 80 extends from an extended end 84 to a connected end 82 having a handle connector 888. A connector extension 862 extends from the outer surface of the urine collector 14 and has a collector-connector configured to connect with the handle-connector 888 to form the dove tail connection 888. Note that the handle is coupled proximal to the top 16 of the urine collector to enable easy positioning of the urine collector through a person's legs for placement for urine collection over a toilet. Also, note the curvature of the handle, having an upward extension portion 89 to provide better control and positioning of the handle over the front portion of a toilet during use.

As shown in FIGS. 1 and 2, a connector 57 may be configured between the retainer portion 50 and the collection funnel portion 60 to enable these two components to be detachably attached. As described herein, a connector may be threads, such as male threads that thread into female threads, a snap on connector, such as a rim that snaps over a flange ring and the like.

As shown in FIG. 2, the urine collector 14 has an interior surface 54 along the collection funnel portion to funnel urine down into the retainer portion. The urine collector 14 has an exterior surface 52 and the retainer portion 50 of the urine collector 14 may have an exterior surface that is cylindrical in shape. The collection funnel portion has a top opening 69 and exterior surface 67 that may be tapering or funneling from the collector opening down to the connected end 65 with the retainer portion 50. The lid also has an exterior surface and an interior surface.

Referring now to FIGS. 3 to 5, the handle 80 is detachably attachable to the urine collector 14, by a dove tail connection 880. As shown in FIG. 3, a collector-connector 868 has a pair of receiver slots 867, 867' along a dove-tail extension 865 and dove-tail flanges 866, 866' extending over the dove-tail extension to form said receiver-slots and the dove-tail 860. A dove-tail stop 864 is configured at the end of the receiver slots. The collector-connector 868 is configured on an extended end of a connector extension 862 that extends from the urine collector 14 and more particularly the tapered end 64 of the collection funnel portion 60 of the urine collector. As shown in FIG. 4, the handle 80 has a handle-connector 888 configured to detachably attach with the collector-connector 868. The handle-connector 888 is configured on the connected end 82 of the handle 80 and has a pair of dove-tail slot-flanges 886, 886 extending inward along a handle-cavity 887 and configured for insertion into the receiver slots 867, 867', respectively of the collector-connector 868. An insertion gap 889 between the two dove-tail slot flanges slides over the dove-tail extension 865 of the collector-connector and the two dove-tail slot-flanges 886, 886' extend within the respective receiver slots 867, 867' to form the dove-tail connection 880 shown in FIG. 5. The two dove-tail slot-flanges 886, 886' abut against the dove-tail stop 864 to secure the handle to the urine collector 14 for picking up the urine collector and positioning it for urine collection.

Figure 6:
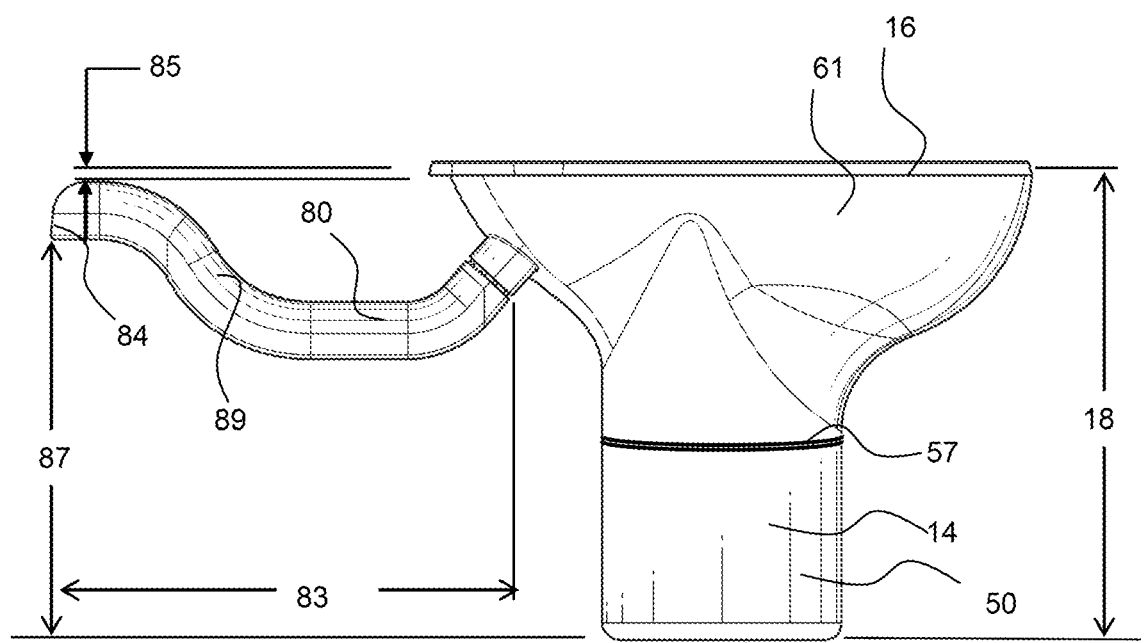
FIG. 6 shows a left side view of the urine collector with a lid over the top opening and a handle detachably attached to the collector-connector.
Figure 7:
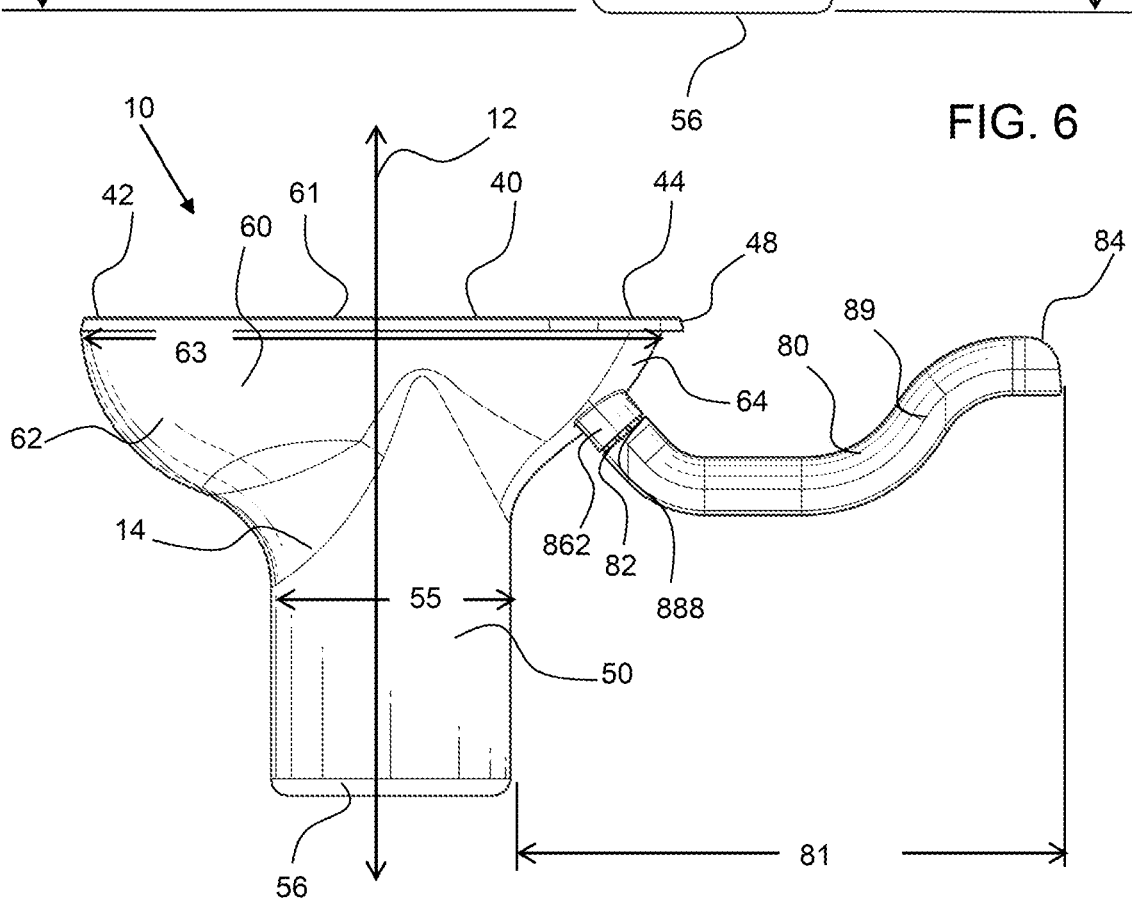
FIG. 7 shows a right side view of the urine collector with a lid over the top opening and a handle detachably attached to the collector-connector.

Referring now to FIGS. 6 and 7, the urine collector 14 has a base 56 at the bottom of the urine collector 14 or the retainer portion 50 of the urine collector. The base is preferably flat or planar so that the urine collector will rest upright on a horizontal surface, even with urine retained therein. Also, the retainer portion 50 has a cross-sectional dimension 55 as measured orthogonal to a vertical axis 12 that is much smaller than the length of the collector opening 61 from the bulbous end 62 to the tapered end 64 of the collection funnel portion 60. Again, this reduction is dimension from the collection funnel portion 60 to the retainer portion 50, for retaining the urine, enables the urine collector to be more easily inserted through the legs of person sitting on toilet for positioning the urine collector under them for urine collection. The gap between the toilet and the person is small and this shape greatly improves ease of use. The retainer portion 50 may be cylindrical and the cross-sectional dimension 55 may be a diameter. The cross-sectional dimension 55 of the retainer portion 50 may be a fraction of the length 63 of the collection funnel portion along the collector opening 61 such as about 0.80 or less, about 0.50 or less, about 0.35 or less and any range between and including the values provided.

As shown in FIG. 6, the extended end 84 of the handle 80 is configured n base-offset distance 87 from the base 56 of the urine collector 14. This base-offset distance may 87 may be equal to or similar to the height 18 of the urine collector as measure from the base 56 to the collector opening 61 and may be about 90% or more of the height 18, about 80% or more of the height 18, about 75% or more of the height or any range between and including the percentages provided. Again, this geometry is important as it enables insertion and maneuvering of the urine collector 14 into position. Put another way, the top of the extended end 84 of the handle 80 may be configured a vertical offset distance 85 from the top of the urine collector 14 or the collector opening 61. As described herein, this vertical offset distance may be kept to a minimum to prevent urine from contacting a woman's hand during urine collection. The handle 80 has a length 83 from the connected end 82 to the extended end 84.

As shown in FIG. 7, the extended end 84 of the handle 80 is configured an extended distance 81 from the proximal side of the retainer portion 50, or from the most proximal portion of the base 56. This extended distance may be effectively long enough such as about 8 cm or more, about 10 cm or more, about 12 cm or more about 15 cm or more to enable positioning the collector opening 61 under a woman for urine collection.

FIG. 8 shows a bottom view of the urine collector 14 with the handle 80 detachably attached to the collector-connector. The base 56 is flat and planar as shown.

FIG. 9 shows a top view of the urine collector with a lid over the top opening and a handle detachably attached to the collector-connector. The lid has a pair of lid-handles 48 configured on the tapered end 44 of the lid, or front end of the urine collector 14 for removing the lid for urine collection. As described herein, the lid maybe configured over the urine collector 14 until a urine specimen is collected and then the lid may be reattached for submission of the urine specimen to prevent spills and contact with the urine collected.

FIG. 10 shows a back view of the urine collector 14 with the lid 40 configured over the top opening of the urine collector.

FIG. 11 shows a front view of the urine collector 14 with a lid 40 configured over the top opening and a handle detachably attached to the collector-connector.

FIG. 12 shows a perspective view of the urine collector with a lid over the top opening and a handle detachably attached to the collector-connector.

Figure 13:
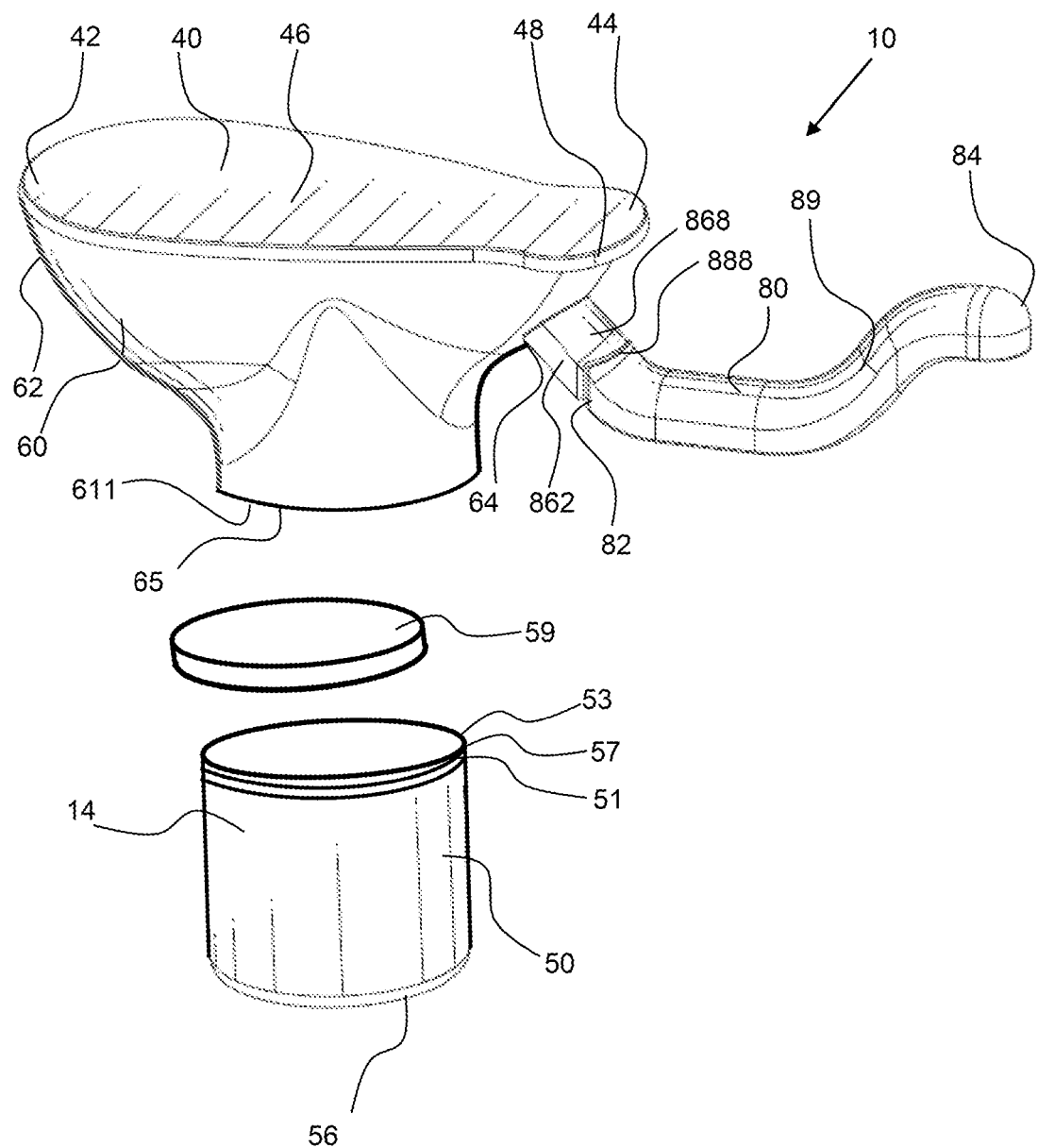
FIG. 13 shows the retainer portion with a retainer portion lid detached from retainer portion and also the retainer portion detached from the collection funnel portion.
Figure 14:
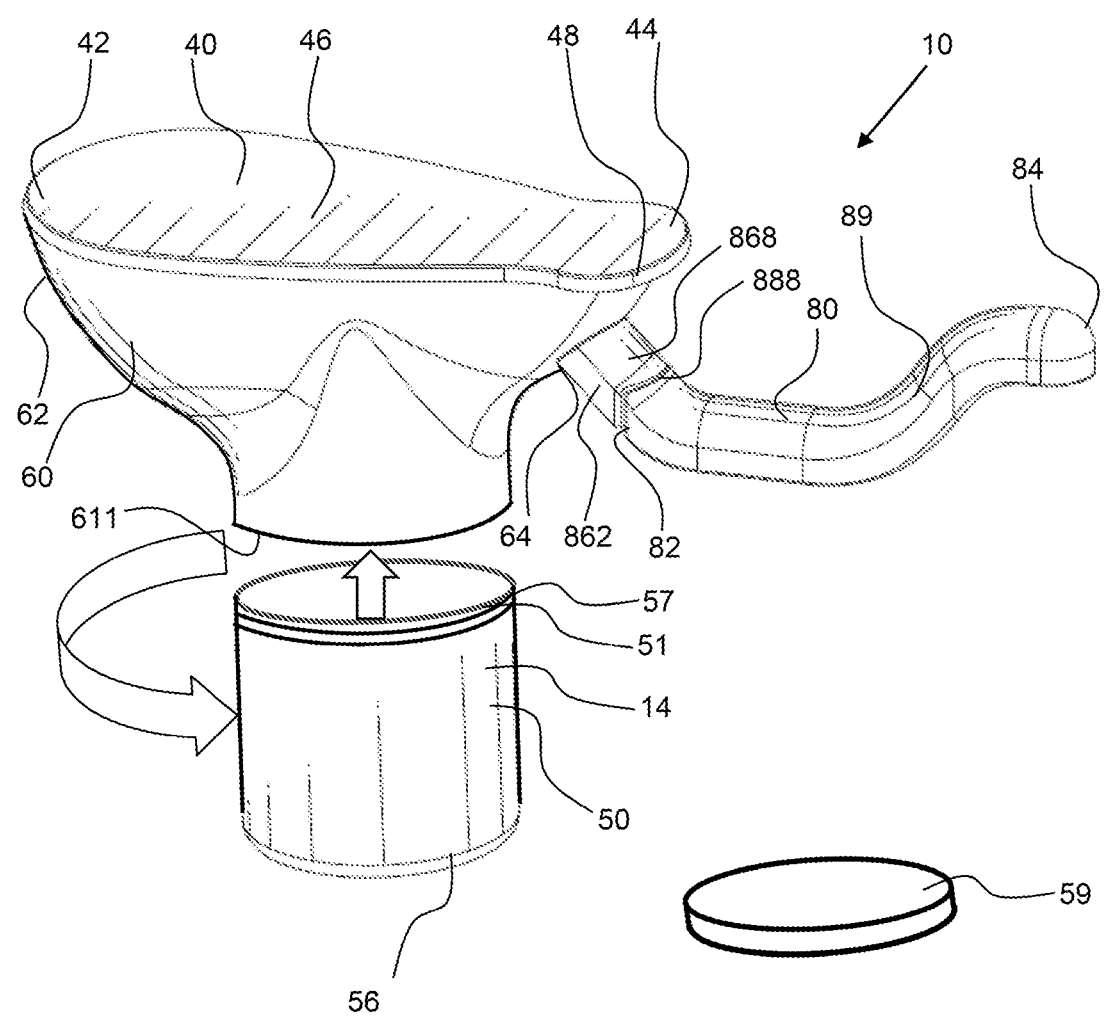
FIG. 14 shows the retainer portion being attached to the collection funnel portion by corresponding threads on the retainer portion and collection funnel portion.

Referring now to FIGS. 13 and 14, the retainer portion 50 may be detachable or detachably attachable to the collection funnel portion 60. The retainer portion 50 may be a cup, such as a cylindrical cup having a retainer portion lid 59 thereon. As shown in FIG. 13, the retainer portion lid is detached from the retainer portion to expose the opening to the retainer portion. The retainer portion connector 57 on the connected end 53 of the retainer portion 50 may be threads 51 that are configured to couple to threads 611 on the connected end 65 of the collection funnel portion 60. As shown in FIG. 14, the retainer portion 50 may be pushed into the collection funnel portion 60 and then turned to couple the threads of the retainer portion with the threads 611 of the collection funnel portion 60, as indicated by the bold arrows. The retainer portion threads 51 may be male threads and the collection funnel portion threads 611 may be female threads.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A urine collection system comprising:
   a) a urine collector comprising;
      i) a collection funnel portion forming a collector opening for receiving urine into the urine collector, said collection funnel portion and said collector opening comprising a bulbous portion and a tapering portion, wherein the tapering portion tapers from the bulbous portion;
      ii) a retainer portion that is coupled to the collection funnel portion and configured to receive urine through the collection funnel portion;
      wherein the collection funnel portion comprising a tapering interior surface from the collector opening to the retainer portion;
   b) a lid configured to cover the collector opening;
   c) a handle consisting of single extension that extends a length along an axis that extends away from the urine collector, from a single connected end, connected to the funnel portion to an extended end
   wherein said handle extends an extended distance from the urine collector; and
   wherein the connected end of the handle is coupled with the tapered portion of the collection funnel portion of the urine collector; and
   wherein the handle is detachably attachable to the urine collector by a dove tail connection and has a handle-connector configured to detachably attach to a collector-connector of the urine collector; and
   wherein the collector connector has a dove tail comprising a dove-tail extension and a pair of dove-tail flanges that extend from the dove tail extension to form receiver-slots along the dove-tail extension.

2. The urine collection system of claim 1, wherein the lid has a bulbous portion and a tapering portion, tapering from the bulbous portion.

3. The urine collection system of claim 1, wherein the handle-connector comprises a pair of dove-tail slot-flanges configured for insertion into the receiver-slots to form said dove-tail connection.

4. The urine collection system of claim 3, wherein the handle-connector has an insertion gap configured between the dove-tail slot-flanges that is configured to extend around the dove-tail extension of the collector-connector.

5. The urine collection system of claim 1, wherein the length of the handle is 10 cm or more.

6. The urine collection system of claim 5, wherein the handle extends a vertical offset distance of 4 cm or less from the collector opening of the urine collector.

7. The urine collection system of claim 6, wherein the handle comprises an upward extension portion between the connected end and the extended end and wherein the upward extension raises the extended end from the connected end.

8. The urine collection system of claim 1, wherein the length of the handle is 15 cm or more.

9. The urine collection system of claim 8, wherein the extended distance of the handle from the urine collector is at least 5 cm.

10. The urine collection system of claim 1, wherein the retainer portion of the urine collector is cylindrical in shape.

11. The urine collection system of claim 1, wherein the retainer portion has a cross-sectional dimension as measured orthogonal to a vertical axis of the urine collector that is no more than 50% of the length of the collection funnel portion along the collector opening.

12. The urine collection system of claim 1, wherein the retainer portion is detachably attachable to the collection funnel portion by a connector.

13. The urine collection system of claim 12, wherein the connector comprises threads in the retainer portion that are configured to thread with threads of the collection funnel portion.

14. A urine collection system comprising:
 a) a urine collector comprising;
  i) a collection funnel portion forming a collector opening for receiving urine into the urine collector, said collection funnel portion and said collector opening comprising a bulbous portion and a tapering portion, wherein the tapering portion tapers from the bulbous portion;
  ii) a retainer portion that is coupled to the collection funnel portion and configured to receive urine through the collection funnel portion;
   wherein the retainer portion has a cross-sectional dimension as measured orthogonal to a vertical axis of the urine collector that is no more than 50% of the length of the collection funnel portion along the collector opening
  iii) a collector-connector;
   wherein the collection funnel portion comprising a tapering interior surface from the collector opening to the retainer portion;
 b) a lid configured to cover the collector opening;
 c) a handle that is detachably attachable to the collector-connector of the urine collector by a dove tail connection, said handle consisting of single extension that extends a length along an axis that extends away from the urine collector, from a single connected end, connected to the funnel portion, to an extended end, and wherein the connect end of said handle includes a handle-connector;
 wherein the connected end of the handle is coupled with the tapered portion of the collection funnel portion of the urine collector; and
 wherein said handle extends an extended distance from the urine collector and a vertical offset distance from the collector opening of less than 4 cm; and
 wherein the collector connector has a dove-tail comprising a dove-tail extension and a pair of dove-tail flanges that extend from the dove-tail extension to form receiver-slots along the dove-tail extension, and wherein the handle-connector comprises a pair of dove-tail slot-flanges configured for insertion into the receiver-slots to form said dove-tail connection.

* * * * *